(12) United States Patent
Drucker et al.

(10) Patent No.: US 7,862,824 B2
(45) Date of Patent: Jan. 4, 2011

(54) ENHANCEMENT OF GLP-2 ACTIVITY OF SUPPRESSING APPETITE

(75) Inventors: Daniel J. Drucker, Toronto (CA); Julie Ann Louise Lovshin, Toronto (CA)

(73) Assignee: 1149336 Ontario, Inc., Toronto, ON (CA)

( * ) Notice: Subject to any disclaimer, the term of this patent is extended or adjusted under 35 U.S.C. 154(b) by 705 days.

(21) Appl. No.: 10/829,201

(22) Filed: Apr. 22, 2004

(65) Prior Publication Data
US 2004/0198642 A1    Oct. 7, 2004

Related U.S. Application Data

(63) Continuation of application No. 10/060,279, filed on Feb. 1, 2002, now abandoned.

(60) Provisional application No. 60/265,329, filed on Feb. 1, 2001.

(51) Int. Cl.
*A61K 38/22*    (2006.01)
*A61K 38/26*    (2006.01)

(52) U.S. Cl. .................................. 424/198.1; 530/308

(58) Field of Classification Search .................. None
See application file for complete search history.

(56) References Cited

U.S. PATENT DOCUMENTS 5,789,379 A * 8/1998 Drucker et al. .............. 514/12
5,912,229 A * 6/1999 Thim et al. ................... 514/12
6,573,291 B2   6/2003 Gronberg et al.

FOREIGN PATENT DOCUMENTS

WO    WO02/066062    8/2002

OTHER PUBLICATIONS

Tang-Christensen et al., "The Proglucagon-derived peptide, glucagon-like peptide-2, is a neurotransmitter involved in the regulation of food intake", Nature America, Inc. -, Nature Medicine, Jul. 2000, vol. 6, pp. 802-807.
Lovshin et al., "Glugan-like Peptide (GLP-2) Action in the Murine Central Nervous System Is Enhanced by Elimination of GLP-1 Receptor Signaling", The Journal of Biological Chemistry, Jun. 2001, vol. 276, No. 24, pp. 21489-21499.

* cited by examiner

*Primary Examiner*—Dong Jiang
(74) *Attorney, Agent, or Firm*—Stoel Rives LLP

(57) ABSTRACT

The effects of GLP-2 are enhanced using a GLP-1 activity inhibitor. For medical use to treat or inhibit the onset of medical conditions, disorder or diseases for which treatment with GLP-2 is indicated, the present invention provides a pharmaceutical combination comprising a GLP-2 activity enhancer, and a GLP-1 activity inhibitor. The combination is useful particularly to treat gastrointestinal conditions such as small bowel syndrome, mucositis and Crohn's disease, and to suppress appetite, for instance to treat obesity.

4 Claims, 7 Drawing Sheets

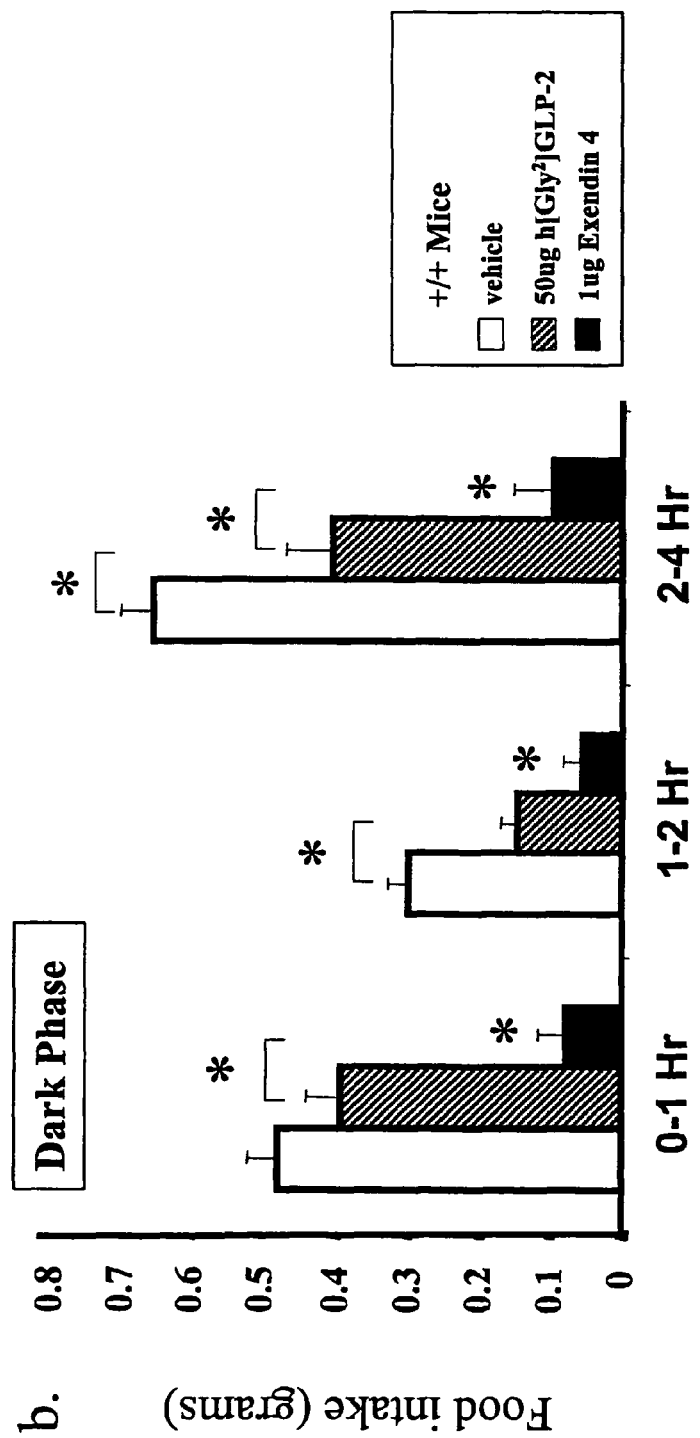

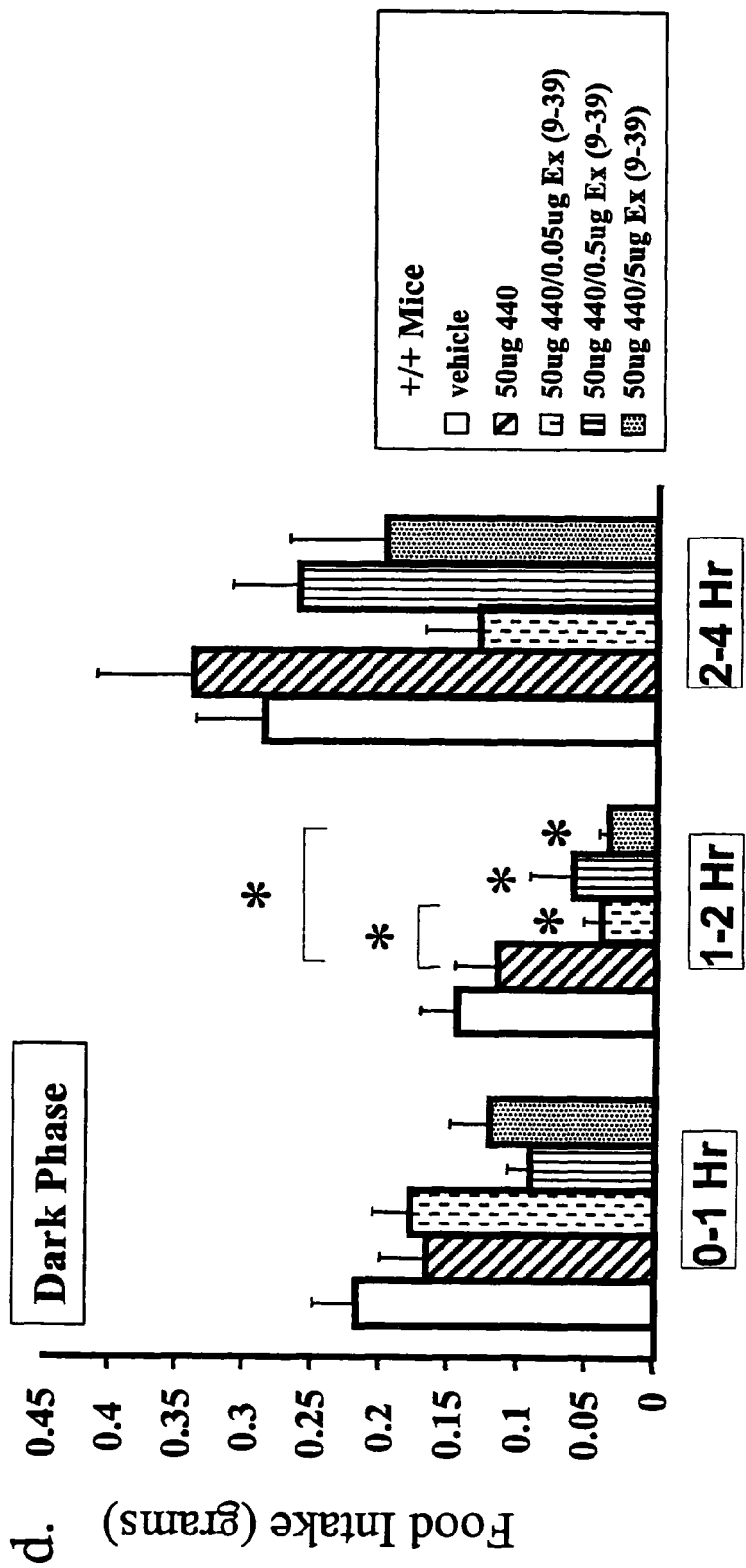

ENHANCEMENT OF GLP-2 ACTIVITY OF SUPPRESSING APPETITE

This is a continuation of application Ser. No. 10/060,279 filed on Feb. 1, 2002, now abandoned, which claims benefit of U.S. provisional application No. 60/265,329 filed on Feb. 1, 2001.

BACKGROUND OF THE INVENTION

1. Field of the Invention

This invention relates to pharmaceutical combinations and methods useful to enhance the activity of glucagon-like peptide 2 (GLP-2) in order to treat or inhibit a variety of medical conditions, disorders and diseases. More particularly, the invention relates to pharmaceutical combinations that modulate activities of glucagon-like peptide 1 (GLP-1) and glucagon-like peptide 2 (GLP-2), for instance to suppress appetite and thereby reduce food intake, for example to treat subjects suffering from obesity, and to enhance gut growth and function to treat gastrointestinal conditions.

2. Background to the Invention

The glucagon-like peptides are liberated in the gut and central nervous system via tissue-specific posttranslational processing of a common proglucagon precursor (1). GLP-1 and GLP-2 are secreted from the gut following nutrient ingestion and regulate nutrient absorption and energy homeostasis (2,3). The actions of glucagon-like peptide-1 (GLP-1) include regulation of gastric emptying, gastric acid secretion, inhibition of food intake and glucagon secretion, and stimulation of glucose-dependent insulin secretion and insulin biosynthesis (2-5). GLP-1 also promotes expansion of islet mass via stimulation of ▢cell proliferation and induction of islet neogenesis via increased ductal pdx-1 expression (6,7). Taken together, these actions of GLP-1 maintain euglycemia, hence enhancing GLP-1 action may represent a useful strategy for the treatment of diabetes mellitus.

Glucagon-like peptide-2 (GLP-2) exhibits trophic properties in the small and large bowel characterized by expansion of the mucosal epithelium predominantly via stimulation of crypt cell proliferation (8-10). GLP-2 also regulates gastric motility, and gastric acid release, intestinal permeability and intestinal hexose transport, actions independent of its effects on epithelial growth (11-14). The intestinotrophic and cytoprotective properties of GLP-2 have been evaluated in the setting of acute intestinal injury, where GLP-2 administration inhibits apoptosis and reduces the severity of mucosal damage in both the small and large intestine (15-18).

In the central nervous system, the glucagon-like peptides are synthesized predominantly in the caudal brainstem and to a lesser extent, in the hypothalamus (19-21). The GLP-1 receptor is expressed more widely throughout the CNS (22, 23), and GLP-1 has been shown to regulate appetite, hypothalamic pituitary function, and the central response to aversive stimulation (24-29). Peripheral administration of GLP-1 or the lizard GLP-1 analogue exendin-4 also reduces food intake and body weight (30,31) suggesting that gut-derived GLP-1 provides signals that influence feeding behavior either directly to the brain, or indirectly, likely via vagal afferents.

In contrast to the increasing number of studies describing CNS actions of GLP-1, much less is known about the potential function(s) of GLP-2 in the brain. Experiments using rat hypothalamic and pituitary membranes demonstrated GLP-2-mediated activation of adenylate cyclase (32). Consistent with these findings, the actions of GLP-2 were subsequently shown to be transduced in a cAMP-dependent manner via a recently cloned GLP-2 receptor (GLP-2R) isolated from hypothalamic and intestinal cDNA libraries (33). The GLP-2R is expressed in a highly tissue-specific manner predominantly in gut endocrine cells, and in the brain (33,34). In comparison with GLP-1, little is known about either the expression or function of the GLP-2R in different regions of the CNS.

Both GLP-1 and GLP-2-immunoreactive fiber tracts project from the brainstem to multiple CNS regions, including the hypothalamus, thalamus, cortex, and pituitary (21,35). Intracerebroventricular (icv) infusion of GLP-2 in rats inhibited food intake (35), (and see WO97/31943 published 4 Sep. 1997), similar to results obtained following icv infusion of GLP-1 (24,36). Unexpectedly, the anorectic effects of GLP-2 in rats were completely inhibited by the GLP-1 receptor antagonist exendin (9-39) (35). These findings implied that CNS GLP-2 may exert its effects via the GLP-1 receptor to inhibit food intake, or alternatively, exendin (9-39) may also function as a CNS GLP-2R antagonist.

It is an object of the present invention to provide a method of medical treatment useful to enhance the medically beneficial effects of GLP-2.

It is another object of the present invention to provide a pharmaceutical combination useful for providing an enhanced GLP-2 effect in subjects for which GLP-2 therapy is indicated.

It is another object of the present invention to provide a method by which the medically beneficial effect of GLP-2 is enhanced.

It is a particular object of the present invention to provide methods of medical treatment, and pharmaceutical compositions therefor, that are useful to regulate appetite, for treatment particularly of subjects suffering from eating disorders and related conditions such as obesity.

SUMMARY OF THE INVENTION

It has now surprisingly been found that GLP-2 activity is enhanced significantly by inhibitors of GLP-1 activity. For use treating medical conditions, disorders and diseases for which treatment with GLP-2 is indicated, the present invention therefore provides, in one aspect, a pharmaceutical combination comprising a first compound that enhances GLP-2 activity, and a second compound that inhibits GLP-1 activity. In another of its aspects, the present invention provides a method useful to treat a medical condition, disorder or disease for which treatment with GLP-2 is indicated, the method comprising the step of treating a subject in need of such treatment with a first compound to inhibit GLP-1 activity, and with a second compound to enhance GLP-2 activity. In combination, such compounds provide a GLP-2 effect that is enhanced significantly relative to the effect seen when either such compound is administered alone.

In embodiments of the present invention, the method of medical treatment and the pharmaceutical combination are exploited particularly to suppress appetite in subjects that are overweight, including subjects suffering from obesity.

These and other aspects and embodiments of the invention are now described in greater detail with reference to the accompanying drawings, in which:

Figure 1:
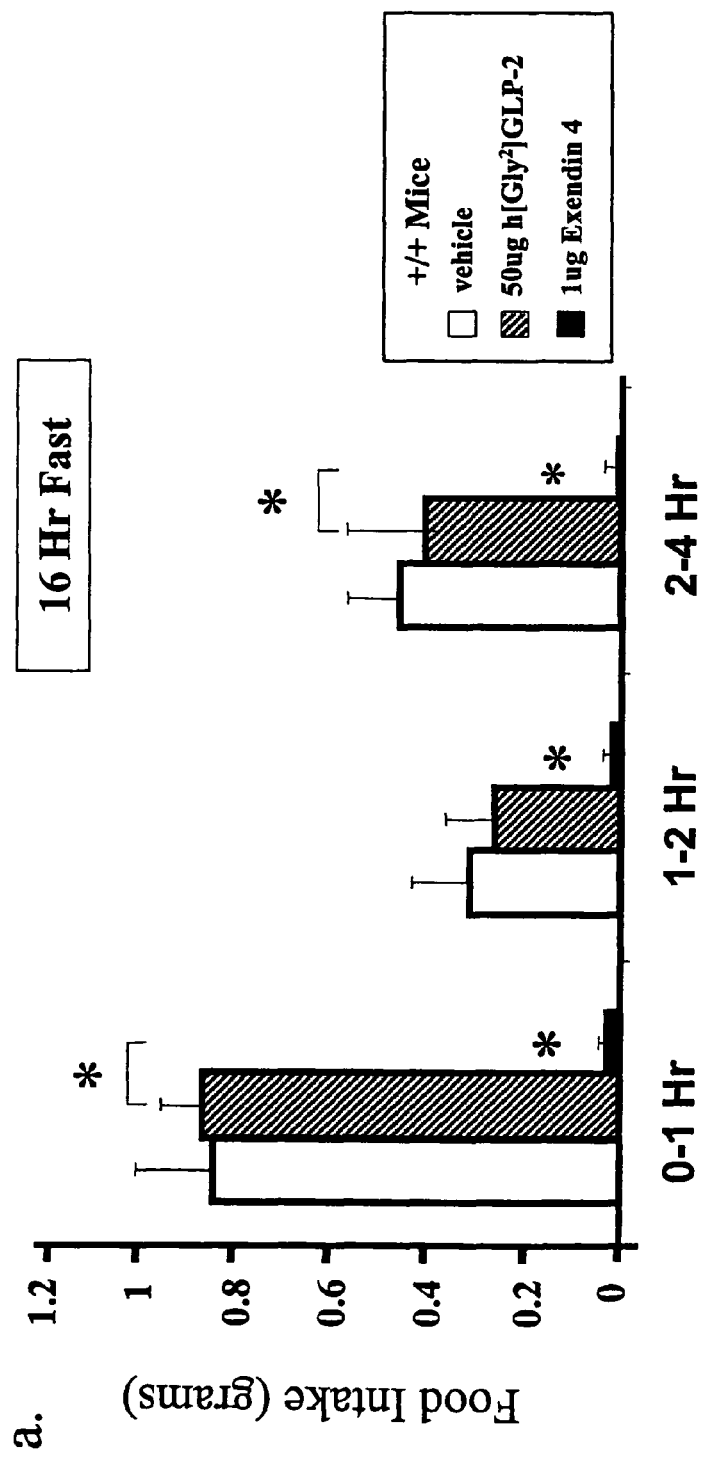
FIG. 1: h[Gly$^2$]-GLP-2 (also designated "440" in the Figure) inhibits dark phase food intake in mice. (a-b) Mice were randomized into three groups and received an icv injection of vehicle (PBS, phosphate-buffered saline), h[Gly$^2$]-GLP-2
Figure 1:
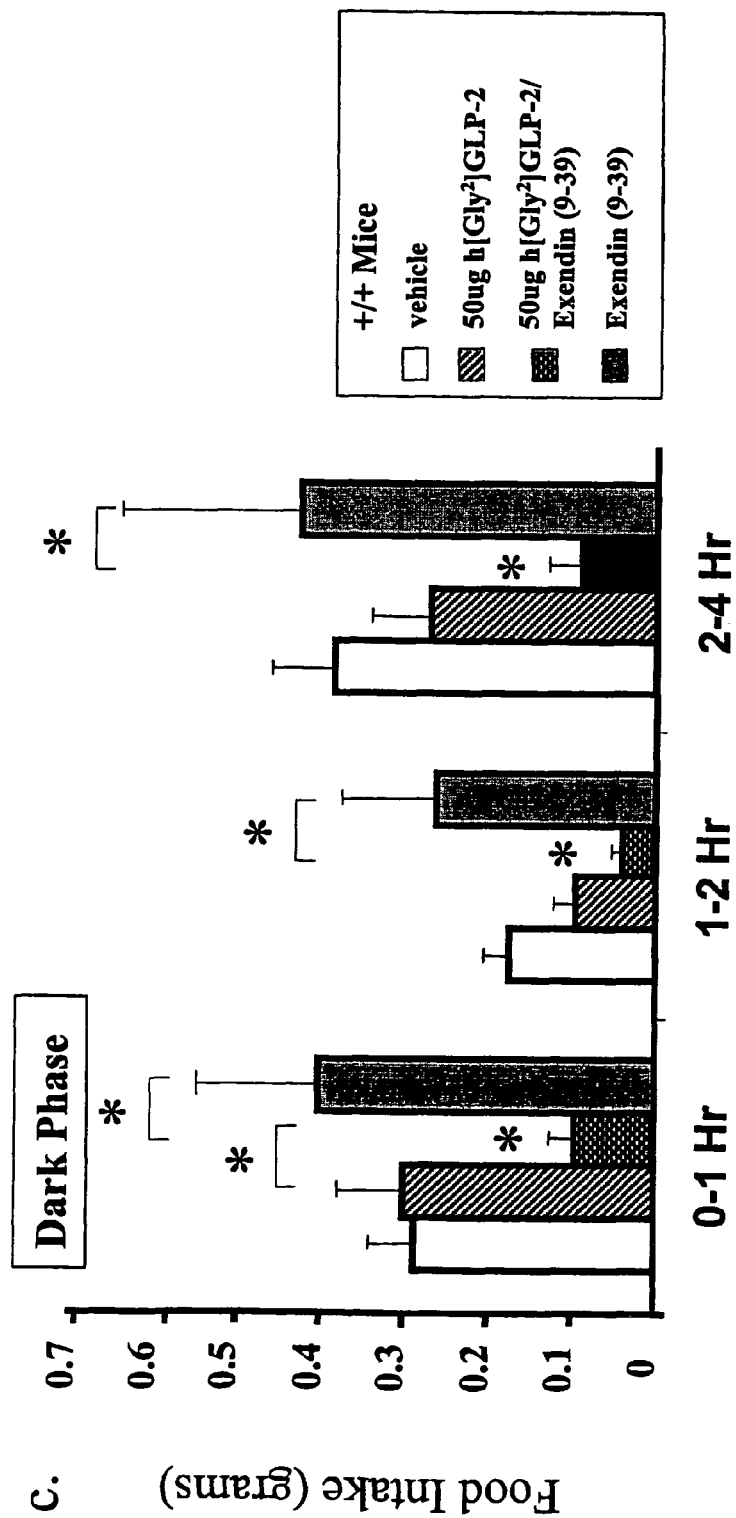
Figure 1:
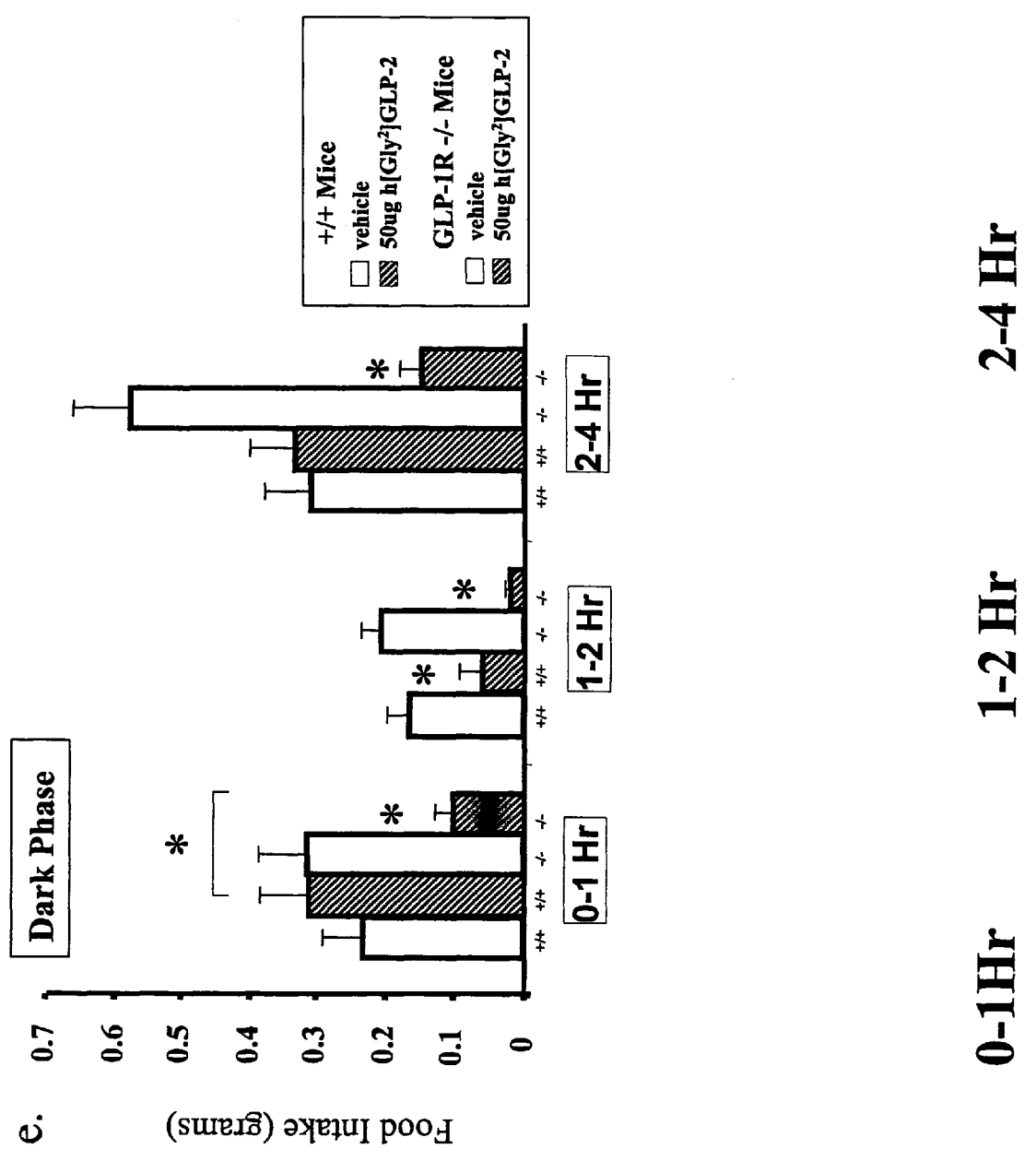

(50 ug dissolved in PBS) or exendin-4 (1 ug dissolved in PBS) following a 15 hour fast (a) or prior to the start of dark phase (b). Following recovery, food intake was measured at 1, 2, and 4 hours (Hr) after injection. Values are expressed as mean±S.E.M., n=6 per group for (a) and n=8-20 for (b). (c) Groups of wildtype mice were administered either vehicle (PBS), h[Gly$^2$]-GLP-2 (50 ug dissolved in PBS), h[Gly$^2$]-GLP-2 and exendin (9-39) (50 ug of each peptide dissolved in PBS) or exendin (9-39) alone (50 ug dissolved in PBS) via icv injection. (f) Groups of wildtype mice were administered (icv) either vehicle (PBS), h[Gly$^2$]-GLP-2 alone (50 ug dissolved in PBS), or h[Gly$^2$]-GLP-2 (50 ug dissolved in PBS) and exendin (9-39) (0.05, 0.5 or 5 ug dissolved in PBS). (e) Groups of wildtype and GLP-1R−/− mice were injected icv with either vehicle (PBS) or h[Gly$^2$]-GLP-2 (50 ug dissolved in PBS) just prior to the start of dark phase and food intake was measured at 1, 2, and 4 hours. Data are expressed as mean±S.E.M., n=5-8 for all groups. Treatments at each time point for experiments shown in FIG. 1 were compared using a one way analysis of variance followed by an LSD multiple range test using SPSS for Windows version 5.0.1 (SPSS Inc., Chicago Ill.). *$p<0.05$ compared to controls (PBS), or to comparisons between groups indicated by connected lines.

Figure 2:
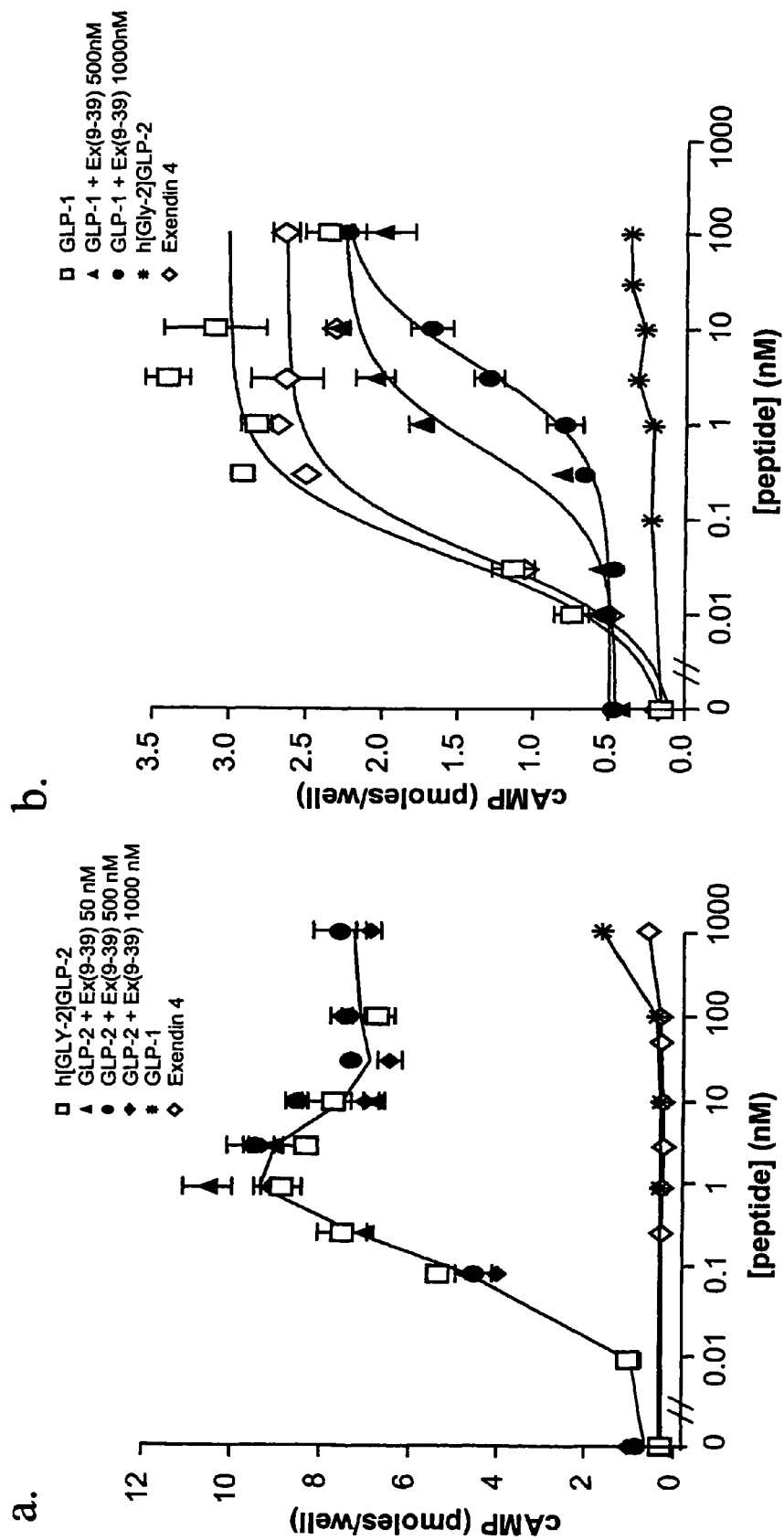

FIG. 2: Exendin (9-39) is a specific GLP-1 receptor antagonist in BHK fibroblasts expressing the cloned GLP-1 receptor. Stably transfected BHK cells expressing either the rat GLP-2 (A) or GLP-1 (B) receptor were pre-treated for 5 minutes with Exendin (9-39) or medium alone before a 10 minute incubation with a receptor agonist; either GLP-1, Exendin-4, or h[Gly$^2$]GLP-2. Peptides were diluted in DMEM containing 100 μM IBMX. The cAMP concentration in aliquots of ethanol extract was determined using a RIA and normalized to show cAMP/well. $EC_{50}$ values for h[Gly$^2$]GLP-2 in the presence of 0, 50, 500, or 1000 nM Exendin (9-39) were 0.044, 0.059, 0.076, and 0.081 nM, respectively. A randomized one-way ANOVA showed no significant difference between pretreatment conditions with exendin (9-39) at all GLP-2 concentrations on the GLP-2R. A randomized two factor ANOVA analysis of the exendin (9-39) antagonism of the GLP-1R showed a significant difference between pretreatment conditions, GLP-1 concentration, and the interaction between them ($p<0.001$ for all groups). The $EC_{50}$ value of GLP-1 alone was 0.041 nM, while in the presence of 500 nM or 1000 nM Exendin (9-39) it was 0.57 and 4.28 nM, respectively. The $EC_{50}$ of Exendin-4 on BHK-GLP-1R cells was 0.041 nM. Graphs show representative data from two separate experiments performed in triplicate. The concentration of peptide is plotted on a logarithmic scale. Error bars represent mean±SD.

Figure 3:
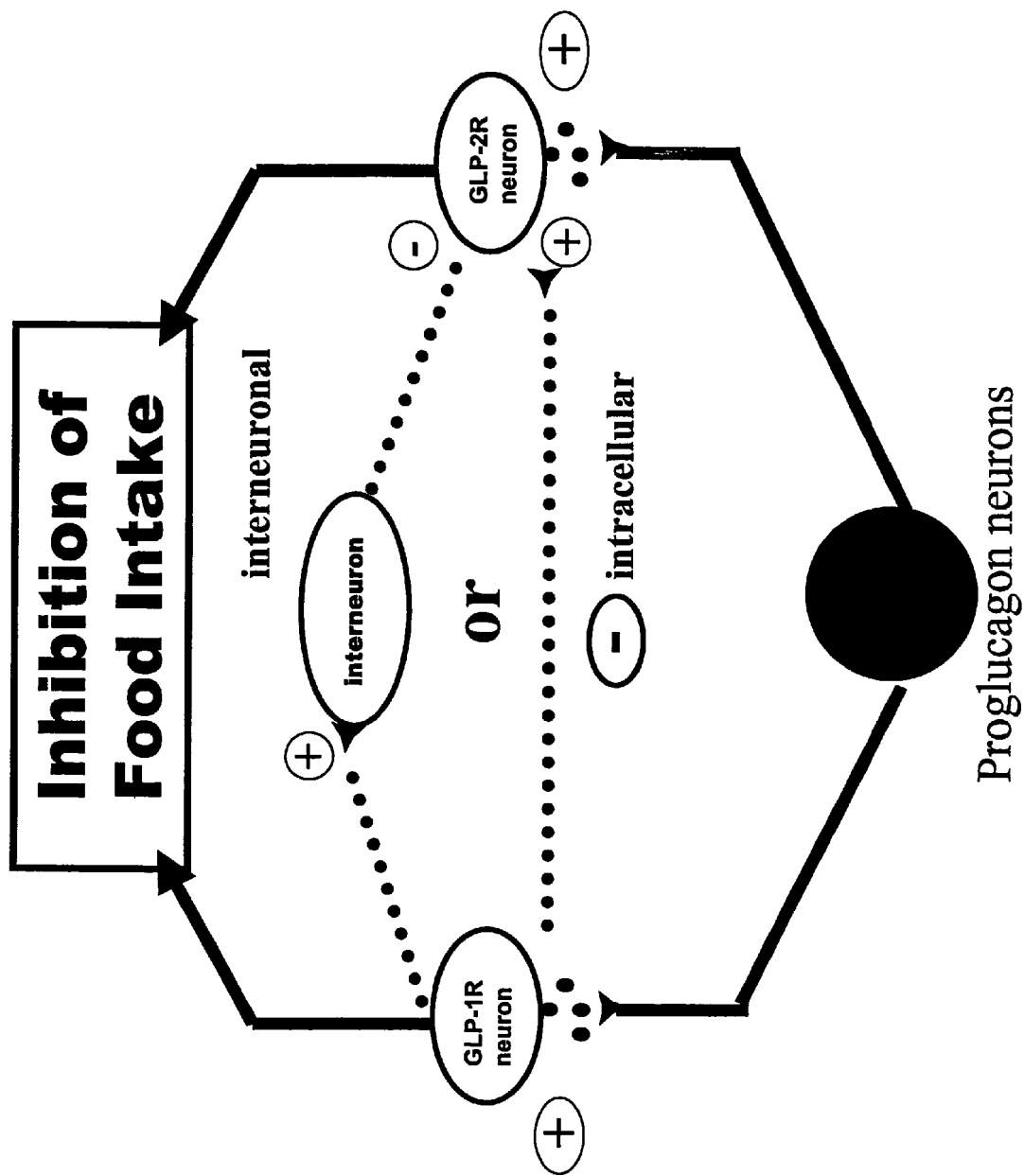

FIG. 3: GLP-1R signaling modulates the inhibitory effects of GLP-2 on food intake pathways in the murine central nervous system. The inhibitory effect of GLP-2 on food intake may be tonically repressed by GLP-1R signaling either through direct intercellular pathways (1) or through or possibly more indirectly through putative intraneuronal pathways (2). Disruption of GLP-1R signaling relieves repression of GLP-2R signaling, resulting in enhanced inhibition of food intake through GLP-2 central pathways. The arrows represent putative synaptic junctions. The positive signs correspond to proposed excitatory synaptic connections, whereas the negative signs correspond to hypothetical inhibitory synaptic connections.

DETAILED DESCRIPTION OF THE PREFERRED EMBODIMENTS

The invention relates to pharmaceutical combinations and uses thereof to treat or inhibit the onset of medical conditions, disorders and diseases for which treatment with GLP-2 is indicated. In accordance with the present invention, such pharmaceutical combinations comprise a GLP-1 activity inhibitor and a GLP-2 activity enhancer.

"GLP-2 activity enhancer" means an agent or compound or treatment modality that enhances GLP-2 activity in vivo. GLP-2 activity enhancers include agents that stimulate GLP-2 receptor signaling, such as GLP-2 receptor agonists and allosteric modulators, as well as agents that stabilize the endogenous activities thereof. GLP-2 activity enhancers also include agents that stimulate GLP-2 receptor activity such as activators of GLP-2 receptor expression. In another respect, the GLP-2 activity enhancers include agents that act to enhance the signaling cascade mediated intracellularly when the GLP-2 receptor is stimulated. Thus, GLP-2 activity enhancers are those compounds, agents or treatment modalities that elevate the activity normally induced by endogenous GLP-2.

In particular embodiments, the GLP-2 activity enhancer is a GLP-2 receptor agonist, including wild type GLP-2 peptides, their analogs and derivatives, and small molecule mimetics thereof. Such agonists include wild type GLP-2 peptides produced naturally by vertebrates such as fish and fowl, and particularly mammals, including human GLP-2, rodent GLP-2 such as mouse GLP-2, degu GLP-2, rat GLP-2, hamster GLP-2 and guinea pig GLP-2, as well as primate GLP-2, equine GLP-2, bovine GLP-2, oxine GLP-2, ovine GLP-2 and goat GLP-2. In addition, such agonists include GLP-2 peptide analogs that incorporate at least one amino acid addition, substitution, deletion or modification, the incorporation of which desirably enhances the stability and/or activity of a counterpart wild type GLP-2. In a particular embodiment of the invention, the GLP-2 receptor agonist is a GLP-2 peptide analog that is modified to confer resistance to cleavage by endogenous enzymes such as DPP-IV. More particularly, the GLP-2 peptide is an analog desirably incorporating an amino acid substitution or modification at one or both of positions 2 and 3, such as a Gly2 analog of GLP-2. In a specific embodiment, the GLP-2 receptor agonist is human Gly2GLP-2 (1-33). Numerous suitable GLP-2 receptor agonists are described in U.S. Pat. No. 5,789,379 and in U.S. Pat. No. 5,990,077. Derivatives of these peptides are also suitable, for instance those that have been derivatized with serum stabilizing fatty acid residues by conjugation to the epsilon amino groups of resident or "knocked-in" lysine residues (see for instance WO98/08872). Still other GLP-2 peptides and analogs can be identified by assessing the selected peptide for example in the food intake assay herein described, and selecting those GLP-2 peptide analogs that elicit a decrease in the food intake of a recipient animal. Similarly, GLP-2 peptides useful as GLP-2 receptor agonists can be identified using the model of GLP-2 induced growth of GI tract tissue, described for instance in the references cited herein and in U.S. Pat. No. 5,990,077 (for small bowel); U.S. Pat. No. 6,051,557 (for upper GI) and CA 2,236,519 (for large bowel). Selection of GLP-2 receptor agonist peptides and small molecules can also be performed at the in vitro level by screening in a GLP-2 receptor-based reporter system described for instance in U.S. Pat. No. 6,077,949.

Other GLP-2 receptor agonists include smaller molecule ligands that trigger at least one GLP-2 receptor signaling pathway. A variety of such agonists are described in WO00/53208 published 14 Sep. 2000.

GLP-2 activity enhancers can also include compounds or agents that prolong the activity of endogenous GLP-2, such as by inhibiting GLP-2 degradation by endogenous proteases. Included among such GLP-2 activity enhancers are inhibitors of dipeptidyl protease (DPP-IV), the endogenous action of which is known to degrade and hence inactivate endogenous GLP-2. It has been shown, for example, that inhibitors of this enzyme enhance the intestinotrophic effect of GLP-2 in rats and mice (see Endocrinology. 2000 November; 141(11): 4013-20, and see U.S. Pat. No. 5,952,301). Examples of DPP-IV inhibitors are described in Archives of Biochemistry and Biophysics, Vol. 323, No. 1, pgs. 148-154 (1995) which discloses certain aminoacylpyrrolidine-2-nitriles; in WO 95/34538 which discloses certain pyrrolidides, phosphonates, azetidines, peptides and azaprolines; in WO 91/16339 which discloses certain tetrapeptide boronic acids; in WO 93/08259 which discloses certain polypeptide boronic acids; and in Bioorganic and Medicinal Chemistry Letters, Vol. 6, No. 22, pgs. 2745-2748 (1996) which discloses certain 4-cyanothiazolidides as inhibitors of DPP-IV. Such inhibitors can be identified routinely by selecting those compounds that prolong the activity of GLP-2 in the presence of the degrading target enzyme.

Also suitable as GLP-2 activity enhancers are compounds that upregulate GLP-2 receptor expression, for instance by interaction with the GLP-2 receptor gene promoter to cause either a triggering of GLP-2 receptor gene expression or a de-repression of that expression, as well as treatment modalities that introduce the GLP-2 receptor, by transgenesis, to the subject undergoing treatment. Methods useful for the introduction of the GLP-2 receptor are described, for instance, in U.S. Pat. No. 6,077,949. Methods useful to screen for agents that regulate activity of the GLP-2 receptor gene promoter are also described, in co-pending U.S. Ser. No. 60/198,909 incorporated herein by reference.

"GLP-1 activity inhibitor" means an agent or compound or treatment modality that inhibits GLP-1 activity in vivo. GLP-1 activity inhibitors include agents that inhibit or antagonize GLP-1 receptor signaling, such as GLP-1 receptor antagonists and allosteric modulators, as well as agents that interfere with production and/or secretion of GLP-1, or the endogenous activity thereof. GLP-1 activity inhibitors also include agents that inhibit GLP-1 receptor activity such as down-regulators of GLP-1 receptor expression. In another respect, the GLP-1 activity inhibitors include agents that act to inhibit or suppress the signaling cascade mediated intracellularly when the GLP-1 receptor is stimulated. Thus, GLP-1 activity enhancers are those compounds, agents or treatment modalities that inhibit the activity normally induced by endogenous GLP-1. In particular embodiments, the GLP-1 activity inhibitor is a GLP-1 receptor antagonist. Included among such antagonists are N-terminally truncated exendin-4 peptides reported for instance in J Biol Chem 1997 Aug. 22; 272(34):21201-6, and particularly including exendin (9-39). Also included are antibodies that bind to either GLP-1 or to the GLP-1 receptor at an epitope that interferes with GLP-1/receptor binding. A system useful to screen for regulators of GLP-1 receptor activity is described for instance in U.S. Pat. No. 5,670,360, incorporated herein by reference.

Also suitable as GLP-1 activity inhibitors are compounds that downregulate or inhibit GLP-1 receptor expression, for instance by interaction with the GLP-1 receptor gene promoter to cause an inhibition of receptor expression. Alternatively, such inhibition of GLP-1 receptor expression can be achieved using anti-sense RNA or DNA having a sequence that binds disruptively to the receptor gene or message to arrest its expression.

In addition, suitable GLP-1 activity inhibitors include compounds that inhibit secretion of GLP-1. For example, somatostatin has the effect of suppressing GLP-1 secretion, and may therefore be used to advantage in reducing endogenous GLP-1 activity (see Am. J. Physiol Endocrinol Metab. 2000 June, 278(6):E1010-8).

In a preferred embodiment, the GLP-1 activity inhibitor is a GLP-1 receptor antagonist. In a specific embodiment, the GLP-1 activity inhibitor is exendin (9-39).

The GLP-1 activity inhibitor and the GLP-2 activity enhancer are useful, in accordance with the present invention, as a pharmaceutical combination to inhibit the onset of and/or treat medical conditions, disorders and diseases for which treatment with GLP-2 is indicated particularly to effect appetite suppression. The term "pharmaceutical combination" embraces physical combinations of the inhibitor and the enhancer. It is to be appreciated, however, that other forms of such combinations are also suitable and are embraced by the term. In one embodiment, for instance, the inhibitor and the enhancer are formulated together. In other embodiments the inhibitor and the enhancer are formulated separately, but associated physically for instance in kit form containing the separate formulations and instructions for their use in combination to treat a target medical condition.

Numerous factors may be taken into consideration by a clinician when determining an optimal dosage for a given subject. Primary among these is the amount of drug (GLP-1 activity inhibitor or GLP-2 activity enhancer) normally produced by the body. Circulating levels of GLP-1 in the body are normally in the range of 2 to 50 picoMoles per liter, depending upon the assay methodology used, and the useful amounts of GLP-1 activity inhibitor will therefore take this GLP-1 concentration into account. Similarly, medically useful amounts of the GLP-2 activity enhancer are those that supplement the endogenous GLP-2 concentration, which is in the range from 10-80 pmol/L in the fasting and fed state, respectively when measured with an assay that assesses intact bioactive GLP-2 peptide (see J Clin Endocrinol Metab. 2000 August; 85(8):2884-8). Assays that assess total GLP-2 plasma immunoreactivity will yield higher values for circulating plasma GLP-2 (see Scand J Clin Lab Invest. 1987 April; 47(2):165-74, and see Gastroenterology. 1999 July; 117(1):99-105).

The dosing regimen will of course be adapted to accommodate the use of those GLP-1 inhibitors that also have a negative effect on endogenous GLP-2 activity. For instance, inhibition of GLP-1 activity using somatostatin to inhibit GLP-1 secretion can also reduce secretion of GLP-2. Thus, when somatostatin is used as a GLP-1 activity inhibitor, an excess of the GLP-2 activity enhancer should be used to account for the GLP-2 activity inhibited by somatostatin. Similarly, when a DPP-IV enzyme inhibitor is used as a GLP-2 activity enhancer, for its stabilizing effect on endogenous GLP-2, a corresponding increase in GLP-1 activity may result, given that DP-IV inhibitors can also stabilize GLP-1. Accordingly, in this case, an excess of GLP-1 activity inhibitor is used, to account for the increase in GLP-1 activity caused by the enzyme inhibitor.

Additional factors include the size of the patient, the age of the patient, the general condition of the patient, the particular disease being treated, the severity of the disease, the presence of other drugs in the patient, the in vivo activity of the peptide or peptide analog and the like. The trial dosages would be chosen after consideration of the results of animal studies and the clinical literature with respect to administration of like drugs. The person of ordinary skill in the art will appreciate that information such as binding constants and Ki derived from in vitro binding competition assays may also be used in calculating dosages.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ ED50. Compounds that exhibit large therapeutic indices are preferred. While compounds that exhibit toxic side effects may be used, care should be taken to design a delivery system that targets such compounds to the site of action, the nervous system, in order to minimize potential damage to other cells and tissues and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from animal studies. A dose may be formulated in animal models to achieve a circulating plasma concentration range that includes the IC50 (i.e., the concentration of the test compound that achieves a half-maximal inhibition of symptoms). Such information can be used to more accurately determine useful doses in humans. Levels in plasma may be measured, for example, by high performance liquid chromatography.

Guidance for determining dosages of exendin (9-39) appropriate for subcutaneous and intravenous administration in humans may be found in the examples herein presented and in the following references: Diabetes. 1999 January; 48(1): 86-93; and J Clin Invest. 1998 Apr. 1; 101(7):1421-30. Preferably, exendin (9-39) is administered to the subject in the range of 1 to 5 pM/kg body weight/minute intravenously, or 0.1 to 5 nM/kg body weight subcutaneously. Delivery of exendin (9-39) directly to the brain may require significantly lower doses, whereas systemic administration of a GLP-1 receptor antagonist to achieve therapeutically useful concentrations in the brain may require higher concentrations.

In the case where the GLP-2 activity enhancer is the preferred human Gly2GLP-2 (1-33) peptide, dosages appropriate for subcutaneous and intravenous administration may also be found in the examples herein presented, in U.S. Pat. No. 5,789,379, and in the references herein listed. For gastrointestinal use, hGly2GLP-2 is suitably administered to the subject by injection of about 1 mL of a suitable formulation in which the hGly2GLP-2 is at a concentration in the range of about 0.1 to about 50 mg/ml, preferably about 5 to about 40 mg/ml more preferably about 7 to about 30 mg/ml, even more preferably about 10 to about 20 mg/ml, and most preferably about 20 mg/ml. Dosing regimens typically will entail the at least once daily, e.g. twice daily, administration of the GLP-2 enhancer for at least about one week, e.g. 10 days or more, followed by maintenance dosing, in the case where GI growth is sought. The dosing regimen and method of administration of GLP-2 that produces therapeutic effects in human subjects is exemplified by studies administering synthetic human GLP-2 to human subjects with short bowel syndrome, wherein patients were administered human GLP-2 as the acetate salt, in a mixture with 0.9% NaCl, buffered with 0.5% ammonia to a neutral pH with acetic acid. Human subjects administered 400 ug of GLP-2 twice daily experienced a significant therapeutic response to the GLP-2 peptide (see Glucagon-like Peptide 2 Improves Nutrient Absorption and Nutritional Status in Short-Bowel Patients With No Colon Gastroenterology March 2001 Volume 120 (in press)). Administration to the brain is anticipated to require significantly lower doses.

Pharmaceutical compositions for use in accordance with the present invention may be formulated in conventional manner using one or more physiologically acceptable carriers or excipients.

Thus, the compounds and their physiologically acceptable salts and solvates may be formulated either individually or in combination for administration by inhalation or insufflation (either through the mouth or the nose) or oral, buccal, parenteral or rectal administration. Additionally, as described below by way of example, compounds for use in the present invention may be delivered directly to the brain.

For delivery directly to the central nervous system, delivery techniques should be preferably designed to cross the blood-brain barrier. For example, agonists and antagonists may be appended to agents which facilitate crossing of the blood-brain barrier (see PCT WO89/10134, which is incorporated by reference herein in its entirety). Alternatively, chemicals can be pre-administered that make the blood brain barrier leaky to let peptides pass. Further, the compounds may be directly delivered to the brain, as shown below by way of a working in vivo example.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented as a kit, for instance in a pack or dispenser device that may contain one or more unit dosage forms containing the active ingredient. The pack may for example comprise metal or plastic foil, such as a blister pack. The pack or dispenser device may be accompanied by instructions for administration.

The pharmaceutical combination of GLP-1 activity inhibitor and GLP-2 activity enhancer is useful, in accordance with another aspect of the present invention, to treat, or prophylactically to inhibit the onset of, the variety of medical conditions, disorder and diseases for which treatment with GLP-2, or its biological equivalent, is indicated. Thus, by addition of the GLP-1 activity inhibitor to a therapeutic regimen that incorporates dosing with a GLP-2 activity enhancer, the medical benefits provided by the GLP-2 activity enhancer are significantly improved. In the GI tract, for instance, the GLP-2 activity enhancer and hence the present combination, can be used trophically to enhance the mass and function particularly of the small bowel, and also of the large bowel and upper GI tract. The present combination is accordingly useful in the treatment and prophylaxis of such conditions as those resulting from intestinal permeability such as bacteremia, as well as ulcers, digestion disorders, malabsorption syndromes, short-gut syndrome, cul-de-sac syndrome, inflammatory bowel disease, celiac sprue, tropical sprue, hypogammaglobulinemic sprue, enteritis, regional enteritis (Crohn's disease), colitis, mucositis, small intestinal damage from toxic or other chemotherapeutic agents, and short bowel syndrome.

In addition, and according to one embodiment of the present invention, the present combination is used to suppress appetite in subjects in need thereof. "Appetite suppression" is revealed as a reduction in food intake in treated subjects relative to an untreated control, as measured for instance by an increase in the duration of fasting or a decrease in the intake of food on a caloric or weight basis. A model useful to assess the appetite suppression effects of a GLP-1 activity inhibitor and/or a GLP-2 activity enhancer is described herein.

In embodiments of the invention, such treatment is effected by administering the GLP-1 activity inhibitor and the GLP-2 activity enhancer either simultaneously or sequentially to the subject. In general, the GLP-2 activity enhance is administered using a dosing regimen effective to realize the desired medical effect, and the GLP-1 activity inhibitor is administered using a dosing regimen effective to improve that effect.

In embodiments, the effects of the inhibitor and the enhancer overlap in the subject, so that the inhibitor and enhancer act simultaneously. Depending on the pharmacokinetics of the selected drug compounds and other established parameters, this may require that the two drugs are administered simultaneously, or may allow for sequential administration provided the first administered compound remains active until the second is administered and for a therapeutic period thereafter.

Subjects that stand to benefit particularly from this pharmaceutical combination therapy are those suffering from conditions and disorders that result from persistently and inappropriately elevated nutrient intake or patients with body weight control disorders, including subjects suffering from obesity. Such subjects include livestock, pets, and other mammals including humans. When selecting the particular GLP-2 activity enhancer, it is desirable to consider the prevalence of GLP-2-degrading enzymes normally present in the circulation of the recipient. Particularly, in rats for instance, DPP-IV enzyme levels are relatively higher than in humans, and it is therefore prudent in rats either to use a GLP-2 peptide in relatively higher doses, or to use a GLP-2 activity enhancer such as Gly2GLP-2 that is rendered resistant to DPP-IV cleavage.

Thus, in one embodiment, the present invention comprises a method for treating an obese subject, the method comprising the step of administering to the subject a pharmaceutical combination of a GLP-2 activity enhancer and a GLP-1 activity inhibitor. The combination therapy is expected to entail the repeated administration, and maintenance dosing, of the patient with the pharmaceutical combination in order to maintain control over the subject's appetite and thereby reduce the obese condition. In some cases, obese or overweight subjects may require a temporary reduction in appetite and achievement of weight loss, for example, prior to surgery to reduce the risk of per- and postoperative complications. In other cases, a more sustained reduction in weight may be desirable in individuals with body weights greater than 30% over normal, as can be assessed by measurement of body mass index. Of particular importance is the treatment of obesity and hyperphagia associated with metabolic diseases such as diabetes. In other cases, women with obesity, insulin resistance, and polycystic ovary syndrome may require reduction in body weight to achieve resumption of normal menses and ovulation.

Embodiments of the invention and methodologies useful in the practise thereof are now described in the following examples.

EXAMPLES

Experimental Procedures

All animal experiments were approved and carried out strictly in accordance with the Canadian Council on Animal Care guidelines and the Animal Care Committee at the Toronto General Hospital, University Health Network, (Toronto, ON). Animals were allowed to acclimatize to the animal care facilities for at least one week prior to any experimental procedure.

Peptides

Recombinant h[Gly$^2$]-GLP-2, a DP IV-resistant GLP-2 analogue (40,41) was a gift from NPS Allelix Corp. (Mississauga, Ontario). Rat GLP-1 (7-36)NH$_2$, Exendin-4, and Exendin (9-39) were purchased from California Peptide Research Inc. (Napa, Calif.). Forskolin and 3-isobutyl-1-methylxanthine (IBMX) were obtained from Sigma Chemical Co., (St. Louis, Mo.).

Analysis of GLP-2R Signaling in BHK-GLP-2R Cells

Baby hamster kidney fibroblast (BHK) cells stably transfected with either the rat GLP-1 or GLP-2 receptors were propagated as previously described (42) and levels of intracellular cAMP were assayed following exposure to individual peptides in DMEM containing 100 μM IBMX (Sigma Chemical Co., St. Louis, Mo.) as reported (41,42). Cells were incubated for 5 minutes with exendin (9-39) or medium alone before addition of an agonist (GLP-1, h[Gly$^2$]GLP-2, or exendin-4). The treated cells were then incubated at 37° C. for 10 minutes. Absolute ethanol (−20° C.) was added to terminate the reaction and the plates were stored at −80° C. until the cell extracts were collected (2-4 hours later). Forskolin was used as a positive control. Cyclic adenosine monophosphate (cAMP) radioimmunoassays (Biomedical Technologies, Stoughton, Mass.) were performed on dried aliquots of extract and data was normalized to cAMP/well. All treatments were performed in triplicate or quadruplicate and the data is expressed as mean±SD. $EC_{50}$ values were calculated using GraphPad Prism 3.00 (GraphPad Software Inc., San Diego, Calif.).

Intracerebroventricular Peptide Injections and Food Intake

For icv injections adult male CD1 mice randomized into multiple experimental groups were deeply anesthetized by inhalation of methoxyflurane (Metophane; Janssen, Toronto Ontario) (43). Following icv injections of equal volumes of saline or peptide dissolved in saline, animals were allowed to recover for ~15-20 minutes until the observation of a righting-response. Mice were then weighed, given a premeasured quantity of rodent chow and food intake was quantified at 1, 2, 4 and 22 hours. The accuracy of icv injection was verified at autopsy analysis by detection of bromophenol dye in the lateral ventricles of selected animals. Animals were injected with peptide at either 19:00 hours (for dark phase feeding studies) or at 10:00 hours following an overnight fast of 15 hours (for fasting studies).

Results

As intracerebroventricular GLP-2 administration inhibited dark phase feeding in rats (35), we compared the effects of a DP IV-resistant GLP-2 analogue, h[Gly$^2$]-GLP-2 (40) with the GLP-1 analogue, exendin-4 on feeding after a prolonged fast, or during dark phase feeding in mice. The GLP-1 analogue exendin-4, but not h[Gly$^2$]-GLP-2, inhibited food intake in fasted mice (FIG. 1a). In contrast, both exendin-4 and h[Gly$^2$]-GLP-2 significantly inhibited dark phase food intake (FIG. 1b), although the inhibitory effects of exendin-4 were significantly more potent than those of the GLP-2 analogue. Similarly, whereas the inhibitory effects of exendin-4 were sustained over 24 hours, the inhibitory effects of h[Gly$^2$]-GLP-2 on food intake were transient and not detectable after more than 4 hours (data not shown).

The effects of GLP-2 on food intake in rats were completely blocked by the GLP-1 receptor antagonist exendin (9-39), suggesting that exendin (9-39) is a functional GLP-2 antagonist in vivo (35). Remarkably, the inhibitory effects of icv h[Gly$^2$]-GLP-2 on food intake in wildtype mice were significantly more pronounced in the presence of co-administered exendin (9-39) at multiple time intervals (FIG. 1c), including the first hour. In contrast, in the absence of exendin (9-39), icv h[Gly$^2$]-GLP-2 did not inhibit food intake in the first hour after peptide injection (FIGS. 1b,c). Furthermore, as little as 0.05 ug of exendin (9-39) was sufficient for significant potentiation of the anorectic effects of h[Gly$^2$]l-GLP-2 on the inhibition of dark phase food intake at the 1-2 hour time point (FIG. 1d).

The demonstration that the GLP-1 receptor antagonist exendin (9-39) significantly enhances the anorectic effect of GLP-2 in wildtype mice implied a role for GLP-1 receptor signaling in the regulation of CNS GLP-2 action. Accordingly, we next examined the effects of icv h[Gly$^2$]-GLP-2 in mice with complete genetic disruption of GLP-1 receptor signaling (43). Remarkably, GLP-1R−/− mice exhibited a significantly greater sensitivity to the inhibitory actions of the GLP-2 analogue on food intake, as can clearly be seen at the 0-1 hour and 2-4 hour time points, compared to the anorectic effects of an identical amount of icv h[Gly$^2$]-GLP-2 administered in +/+ control mice (FIG. 1e). These findings illustrate, through two different experimental approaches that inhibition of GLP-1 receptor signaling using peptide antagonists, or using a genetic approach to disrupt GLP-1 receptor expression, is consistently associated with enhancement of GLP-2 action in the CNS.

As the GLP-2-mediated inhibition of food intake was blocked by the GLP-1 receptor antagonist exendin (9-39) in rats (35), we examined whether exendin (9-39) functioned as a rat GLP-2 receptor antagonist using cells expressing the cloned rat GLP-2 receptor in vitro. Although h[Gly$^2$]-GLP-2 increased cAMP accumulation in a dose-dependent manner in BHK-GLP-2R cells, increasing amounts of exendin (9-39), from 50-1000 nM had no effect on h[Gly$^2$]-GLP-2-stimulated cAMP formation (FIG. 2). Furthermore, the GLP-2R responded specifically to h[Gly$^2$]-GLP-2 as no cAMP accumulation was detected following incubation of BHK-GLP-2R cells with GLP-1 or exendin-4 (FIG. 2a). In contrast, exendin (9-39) decreased GLP-1-stimulated cAMP accumulation in a concentration-dependent manner in BHK-GLP-1R cells (FIG. 2b), consistent with its known actions as a GLP-1 receptor antagonist. Furthermore, the actions of h[Gly$^2$]-GLP-2 were specific for cells expressing the GLP-2 receptor, as h[Gly$^2$]GLP-2 had no effect on cAMP accumulation in BHK-GLP-1R cells (FIG. 2).

Discussion

Several lines of evidence support a role for glucagon-like peptides in the control of food intake. Intracerebroventricular administration of GLP-1 agonists inhibits food intake in mice and rats (24,36,43), whereas peripheral administration of GLP-1 reduces appetite and size of meal ingestion in human subjects (30,49). Furthermore, intracerebroventricular administration of the GLP-1 receptor antagonist exendin (9-39) increases food intake in short term studies (24), and promotes weight gain in rats after 6 days of icv administration in vivo (50). Nevertheless, GLP-1 receptor−/− mice are not obese, do not eat more than wildtype mice, and fail to develop obesity even following several months of high fat feeding (43,51). Hence it remains unclear whether the anorectic effects of icv GLP-1 represent a highly specific effect on CNS feeding centers, or a non-specific effect on CNS nuclei that mediate the response to aversive stimulation (29,52-55). The available evidence suggests that although icv GLP-1 transiently inhibits food intake (52), GLP-1 does not appear to be an essential regulator of long term body weight homeostasis in vivo.

The recent report that intracerebroventricular injection of GLP-2 inhibits food intake in rats (35) provides new information about a possible role for GLP-2 in the CNS. Furthermore, the data clearly show that the effect of GLP-2 on dark phase food intake is not blocked but is significantly enhanced in wildtype mice in the presence of exendin (9-39), a GLP-1 receptor antagonist (56).

Consistent with the results obtained in wildtype mice following GLP-1 receptor blockade with exendin (9-39), GLP-2 more potently inhibited food intake in GLP-1R−/− compared to control wildtype mice. Hence the data clearly demonstrate that in contrast to results obtained in rats (35), the effects of GLP-2 on food intake in mice are not attenuated by disruption of GLP-1 receptor signaling. Moreover, transient blockade of the GLP-1 receptor with exendin (9-39) or complete disruption of GLP-1R signaling in GLP-1R−/− mice was associated with enhanced sensitivity to the inhibitory response to GLP-2.

The data in wildtype mice co-injected with h[Gly$^2$]-GLP-2 and exendin (9-39), taken together with studies using cloned GLP-2 and GLP-1 receptors, clearly demonstrates that exendin (9-39) is not a functional antagonist of the GLP-2 receptor in vivo or in vitro. Furthermore, the demonstration that h[Gly$^2$]-GLP-2 inhibits food intake in GLP-1R−/− mice, taken together with the enhanced sensitivity to GLP-2 action following inhibition of GLP-1 signaling, provides new evidence demonstrating that the effects of GLP-2 on feeding do not require the GLP-1 receptor but may be modulated in part through the functional activity of GLP-1 receptor signaling.

The data generated using the GLP-1 receptor antagonist exendin (9-39) and GLP-1R−/− mice, also clearly show that blockade or disruption of GLP-1 signaling enhances the sensitivity to GLP-2 action in the murine CNS.

The citations listed hereinafter are useful to an understanding of the present invention and related methodologies, and are incorporated herein by reference in their entirety.

1. Mojsov, S., Heinrich, G., Wilson, I. B., Ravazzola, M., Orci, L., and Habener, J. F. (1986) *J Biol Chem* 261, 11880-11889
2. Drucker, D. J. (1998) *Diabetes* 47, 159-169
3. Drucker, D. J. (2001) *Endocrinology* 142, 521-527
4. Hoist, J. J. (1999) *Trends in Endocrinology and Metabolism* 10(229-235)
5. Kieffer, T. J., and Habener, J. F. (1999) *Endocr Rev* 20(6), 876-913
6. Xu, G., Stoffers, D. A., Habener, J. F., and Bonner-Weir, S. (1999) *Diabetes* 48(12), 2270-6
7. Stoffers, D. A., Kieffer, T. J., Hussain, M. A., Drucker, D. J., Egan, J. M., Bonner-Weir, S., and Habener, J. F. (2000) *Diabetes* 49, 741-748
8. Drucker, D. J., Ehrlich, P., Asa, S. L., and Brubaker, P. L. (1996) *Proc Natl Acad Sci USA* 93, 7911-7916
9. Tsai, C.-H., Hill, M., and Drucker, D. J. (1997) *Am J Physiol* 272, G662-G668
10. Tsai, C.-H., Hill, M., Asa, S. L., Brubaker, P. L., and Drucker, D. J. (1997) *Am J Physiol* 273, E77-E84
11. Wojdemann, M., Wettergren, A., Hartmann, B., and Holst, J. J. (1998) *Scand. J. Gastroenterol.* 33, 828-832
12. Wojdemann, M., Wettergren, A., Hartmann, B., Hilsted, L., and Hoist, J. J. (1999) *J Clin Endocrinol Metab* 84(7), 2513-7
13. Benjamin, M. A., McKay, D. M., Yang, P.-C., and Perdue, M. H. (2000) *Gut* 47, 112-119
14. Cheeseman, C. I., and Tsang, R. (1996) *Am J Physiol Gastrointest Liver Physiol* 271, G477-G482
15. Drucker, D. J., Yusta, B., Boushey, R. P., Deforest, L., and Brubaker, P. L. (1999) *Am. J. Physiol* 276, G79-G91
16. Boushey, R. P., Yusta, B., and Drucker, D. J. (1999) *Am J Physiol* 277, E937-E947
17. Alavi, K., Schwartz, M. Z., Palazzo, J. P., and Prasad, R. (2000) *J Pediatr Surg* 35(6), 847-51
18. Prasad, R., Alavi, K., and Schwartz, M. Z. (2000) *J Pediatr Surg* 35(2), 357-9
19. Drucker, D. J., and Asa, S. (1988) *J Biol Chem* 263, 13475-13478
20. Han, V. K. M., Hynes, M. A., Jin, C., Towle, A. C., Lauder, J. M., and Lund, P. K. (1986) *J. Neurosi. Res.* 16, 97-107
21. Larsen, P. J., Tang-Christensen, M., Holst, J. J., and Orskov, C. (1997) *Neuroscience* 77, 257-270
22. Merchenthaler, I., Lane, M., and Shughrue, P. (1999) *J Comp Neurol* 403(2), 261-80
23. Campos, R. V., Lee, Y. C., and Drucker, D. J. (1994) *Endocrinology* 134, 2156-2164
24. Turton, M. D., O'Shea, D., Gunn, I., Beak, S. A., Edwards, C. M. B., Meeran, K., Choi, S. J., Taylor, G. M., Heath, M. M., Lambert, P. D., Wilding, J. P. H., Smith, D. M., Ghatei, M. A., Herbert, J., and Bloom, S. R. (1996) *Nature* 379, 69-72
25. Beak, S. A., Heath, M. M., Small, C. J., Morgan, D. G. A., Ghatei, M. A., Taylor, A. D., Buckingham, J. C., Bloom, S. R., and Smith, D. M. (1998) *J Clin Invest* 101, 1334-1341
26. Beak, S. A., Small, C. J., Ilovaiskaia, I., Hurley, J. D., Ghatei, M. A., Bloom, S. R., and Smith, D. M. (1996) *Endocrinology* 137, 4130-4138
27. Seeley, R. J., Blake, K., Rushing, P. A., Benoit, S., Eng, J., Woods, S. C., and D'Alessio, D. (2000) *J Neurosci* 20(4), 1616-21
28. Seeley, R. J., Woods, S. C., and D'Alessio, D. (2000) *Endocrinology* 141(2), 473-475
29. Rinaman, L. (1999) *Am J Physiol* 277(2 Pt 2), R582-90
30. Toft-Nielsen, M. B., Madsbad, S., and Holst, J. J. (1999) *Diabetes Care* 22(7), 1137-43
31. Szayna, M., Doyle, M. E., Betkey, J. A., Holloway, H. W., Spencer, R. G., Greig, N. H., and Egan, J. M. (2000) *Endocrinology* 141(6), 1936-41
32. Hoosein, N. M., and Gurd, R. S. (1984) *FEBS Lett.* 178, 83-86
33. Munroe, D. G., Gupta, A. K., Kooshesh, P., Rizkalla, G., Wang, H., Demchyshyn, L., Yang, Z.-J., Kamboj, R. K., Chen, H., McCallum, K., Sumner-Smith, M., Drucker, D. J., and Crivici, A. (1999) *Proc. Natl. Acad. Sci. USA* 96, 1569-1573
34. Yusta, B., Huang, L., Munroe, D., Wolff, G., Fantaske, R., Sharma, S., Demchyshyn, L., Asa, S. L., and Drucker, D. J. (2000) *Gastroenterology* 119(3), 744-755
35. Tang-Christensen, M., Larsen, P. J., Thulesen, J., Romer, J., and Vrang, N. (2000) *Nat Med* 6(7), 802-7
36. Tang-Christensen, M., Larsen, P. J., Goke, R., Fink-Jensen, A., Jessop, D. S., Moller, M., and Sheikh, S. P. (1996) *Am J Physiol* 271, R848-R856
37. White, R. B., Broqua, P., Meyer, J., Junien, J.-L., and Aubert, M. L. (2000) 82nd Annual Meeting of the Endocrine Society Toronto, Ontario, 271:A1115
38. Chomczynski, P., and Sacchi, N. (1987) *Anal Biochem* 162, 156-159
39. Piechaczyk, M., Blanchard, J. M., Marty, L., Dani, C., Panabieres, F., El Sabouty, S., Fort, P., and Jeanteur, P. (1984) *Nucleic Acids Res* 12(18), 6951-63
40. Drucker, D. J., Shi, Q., Crivici, A., Sumner-Smith, M., Tavares, W., Hill, M., Deforest, L., Cooper, S., and Brubaker, P. L. (1997) *Nature Biotechnology* 15, 673-677
41. DaCambra, M. P., Yusta, B., Sumner-Smith, M., Crivici, A., Drucker, D. J., and Brubaker, P. L. (2000) *Biochemistry* 39(30), 8888-8894
42. Yusta, B., Somwar, R., Wang, F., Munroe, D., Grinstein, S., Klip, A., and Drucker, D. J. (1999) *J Biol Chem* 274(43), 30459-67
43. Scrocchi, L. A., Brown, T. J., MacLusky, N., Brubaker, P. L., Auerbach, A. B., Joyner, A. L., and Drucker, D. J. (1996) *Nature Med* 2, 1254-1258
44. Sherwood, N. M., Krueckl, S. L., and McRory, J. E. (2000) *Endocr Rev* 21(6), 619-70

45. Lankat-Buttgereit, B., and Goke, B. (1997) *Peptides* 18, 617-624
46. Galehshahi, F. S., Goke, B., and Lankat-Buttgereit, B. (1998) *FEBS Lett* 436(2), 163-8
47. Wildhage, I., Trusheim, H., Goke, B., and Lankat-Buttgereit, B. (1999) *Endocrinology* 140(2), 624-31
48. Portois, L., Maget, B., Tastenoy, M., Perret, J., and Svoboda, M. (1999) *J Biol Chem* 274(12), 8181-90
49. Gutzwiller, J. P., Drewe, J., Goke, B., Schmidt, H., Rohrer, B., Lareida, J., and Beglinger, C. (1999) *Am J Physiol* 276(5 Pt 2), R1541-4
50. Meeran, K., O'Shea, D., Edwards, C. M., Turton, M. D., Heath, M. M., Gunn, I., Abusnana, S., Rossi, M., Small, C. J., Goldstone, A. P., Taylor, G. M., Sunter, D., Steere, J., Choi, S. J., Ghatei, M. A., and Bloom, S. R. (1999) *Endocrinology* 140(1), 244-50
51. Scrocchi, L. A., and Drucker, D. J. (1998) *Endocrinology* 139, 3127-3132
52. Donahey, J. C. K., Van Dijk, G., Woods, S. C., and Seeley, R. J. (1998) *Brain Research* 779, 75-83
53. Thiele, T. E., Van Dijk, G., Campfield, L. A., Smith, F. J., Burn, P., Woods, S. C., Bernstein, H., and Seeley, R. J. (1997) *Am J Physiol* 272, R726-R730
54. Thiele, T. E., Seeley, R. J., D'Alessio, D., Eng, J., Bernstein, I. L., Woods, S. C., and van Dijk, G. (1998) *Brain Res* 801 (1-2), 164-70
55. Rinaman, L. (1999) *Am J Physiol* 277(5 Pt 2), R1537-R1540
56. Goke, R., Fehmann, H.-C., Linn, T., Schmidt, H., Krause, M., Eng, J., and Gške, B. (1993) *J Biol Chem.* 268, 19650-19655
57. Sivarajah, P., Wheeler, M. B., and Irwin, D. M. (2001) *Comparative Biochemistry and Physiology* in press
58. Traber, P. G., and Silberg, D. G. (1996) *Annu Rev Physiol* 58, 275-97
59. Boylan, M. O., Jepeal, L. I., Jarboe, L. A., and Wolfe, M. M. (1997) *J Biol Chem* 272(28), 17438-43
60. Dusing, M. R., Brickner, A. G., Lowe, S. Y., Cohen, M. B., and Wiginton, D. A. (2000) *Am J Physiol Gastrointest Liver Physiol* 279(5), G1080-93
61. Jin, T., and Drucker, D. J. (1996) *Mol Cell Biol* 16, 19-28
62. Larsen, P. J., Tang-Christensen, M., and Jessop, D. S. (1997) *Endocrinology* 138, 4445-4455
63. MacLusky, N., Cook, S., Scrocchi, L., Shin, J., Kim, J., Vaccarino, F., Asa, S. L., and Drucker, D. J. (2000) *Endocrinology* 141, 752-762
64. Oka, J., Suzuki, E., and Kondo, Y. (2000) *Brain Res* 878(1-2), 194-8
65. van Dijk, G., and Thiele, T. E. (1999) *Neuropeptides* 33(5), 406-14
66. Franklin, K., and Paxinos, G. (1997) *The mouse brain in sterotaxic coordinates*, Academic Press, San Diego

What is claimed is:

1. A pharmaceutical composition useful to suppress the appetite of a subject, the composition comprising $Gly_2GLP-2$ and exendin (9-39).

2. A kit comprising the pharmaceutical composition as defined in claim 1, and instructions for the use thereof to suppress the appetite of a subject.

3. A method for treating a subject to suppress appetite, comprising administering to the subject an effective amount of the pharmaceutical composition according to claim 1.

4. A method for treating a subject to suppress appetite according to claim 3, wherein said subject is an obese subject.

* * * * *